United States Patent [19]

Bewsey

[11] Patent Number: 5,009,710

[45] Date of Patent: Apr. 23, 1991

[54] ALGINATE COMPOSITION FOR APPLICATION TO A SOIL OR PLANT LOCUS

[75] Inventor: John A. Bewsey, Transvaal, South Africa

[73] Assignee: Harvest Chemicals (Proprietary) Limited, South Africa

[21] Appl. No.: 428,432

[22] Filed: Oct. 30, 1989

Related U.S. Application Data

[63] Continuation of Ser. No. 196,627, May 19, 1988, abandoned.

[51] Int. Cl.$^5$ .................... C05B 37/04; C05B 17/00; C05B 3/00
[52] U.S. Cl. ........................................ 106/208; 536/3; 252/2; 252/3; 106/209; 43/132.1; 71/64.09; 71/904; 71/65; 71/DIG. 1
[58] Field of Search ................... 536/3; 514/54, 779, 514/444; 106/162, 208, 209

[56] References Cited

U.S. PATENT DOCUMENTS

| | | | |
|---|---|---|---|
| 2,007,721 | 7/1935 | Lindstaedt | 536/3 |
| 2,420,308 | 5/1947 | Gates | 252/316 |
| 2,441,729 | 5/1948 | Steiner | 99/131 |
| 2,837,479 | 6/1958 | Birchall | 536/3 |
| 3,537,873 | 11/1970 | Degginger | 536/3 |
| 4,401,456 | 8/1983 | Connick, Jr. | 514/522 |

FOREIGN PATENT DOCUMENTS

| | | |
|---|---|---|
| 742436 | 3/1933 | France . |
| 1521308 | 4/1968 | France . |
| 1271575 | 4/1972 | United Kingdom . |
| 1308614 | 2/1973 | United Kingdom . |

OTHER PUBLICATIONS

Chemical Patents Index, Basic Abstracts Journal, Section C, Week 86 36, 29th Oct. 1986, Abstract No. 86-236762/36, Derwent Publications, Ltd., London, GB; and JP-A-61 167 603 (El Kagaku Kogyo K.K.) 29-07-1986, "Abstract".

Hackh's Chemical Dictionary, Fourth Edition, Edited by Julius Grant, McGraw-Hill; New York, pp. 437-438.

Chemical Abstracts, vol. 91, No. 24, Dec. 10, 1979, p. 63, Abstract No. 194910p.

*Primary Examiner*—Johnnie R. Brown
*Assistant Examiner*—Gary L. Kunz
*Attorney, Agent, or Firm*—Lowe, Price, LeBlanc, Becker & Shur

[57] ABSTRACT

A composition for application to a soil or plant locus which contains a major amount of water and a minor amount of an alkaline earth metal alginate gel uniformly dispersed through the water. The composition may include an active ingredient such as a herbicide, pesticide, fungicide, fertilizer or the like. The composition may also contain a suitable wetting agent to assist in spreading it on a surface to which it is applied. The composition, when it contains a foaming agent, has particular application for the control and extinguishing of forest fires.

6 Claims, No Drawings

ALGINATE COMPOSITION FOR APPLICATION TO A SOIL OR PLANT LOCUS

This application is a continuation of application Ser. No. 07/196,627, filed May 19, 1988, now abandoned.

BACKGROUND OF THE INVENTION

This invention relates to an additive for agricultural chemical compositions.

Agricultural chemicals such as herbicides, fertilizers, insecticides, fungicides and the like are applied in a variety of formulations and compositions. The compositions may take the form of dusting powders or granules, dispersible powders or granules, aqueous dispersions or emulsions and sprays and aerosol formulations. The active ingredients for such formulations are dispersed in a variety of mediums or carriers depending on the nature of the formulation.

Alginate gels are derived from seaweed and are used in various food products in a highly purified form, i.e. less than 0.1 percent by weight of insolubles having a particle size greater than 10 microns.

SUMMARY OF THE INVENTION

According to the present invention, there is provided a composition, for application to a soil or plant locus including a gel which comprises a major amount of water and minor amount of an alginate gel matrix uniformly dispersed through the water. The composition thus includes, as an essential component an alginate gel. Water forms the continuous phase and the alginate gel matrix the dispersed phase.

According to another aspect of the invention, there is provided a method of treating a soil or plant locus including the step of applying to that locus a composition described above.

DETAILED DESCRIPTION OF THE INVENTION

It has been found that the composition adheres well to surfaces such as soil, and leaves and other foliage of plants. These adherent or sticking properties of the composition allow it to be used in a number of applications. For example, the composition contains a considerable amount of water and that water is retained on the surface to which the composition has been applied for a long period. This property may be used for fighting fires or preventing the spread of fires in forests and other agricultural areas. Active ingredients such as herbicides, fertilizers, insecticides, fungicides, and the like may be included in the composition. These active ingredients will be retained on the surface to which the composition has been applied.

The composition has particular application for sprays. The alginate gel of the composition is thixotropic which means that although it is thick and viscous, it will spray easily either from the ground or from the air at high concentrations. Due to the polymer structure of this gel, spray particles of a uniform size are produced and "drift" i.e. sub-micron sized spray particles, is substantially reduced. The composition may be used for spraying herbicides, pesticides, fertilisers and foliar compositions.

The water will generally be present in the gel in an amount of at least 90 percent by weight, and the alginate gel matrix will generally be present in an amount of up to 5 percent by weight of the gel.

The alginate gel matrix is preferably an alkaline earth metal alginate gel matrix. The preferred alkaline earth metals are calcium, magnesium and mixtures thereof. The gel may be formed by bringing together a solution of a soluble alginate, for example, sodium alginate, and a dispersion of a finely divided, poorly soluble alkaline earth metal salt. It is important that in producing the gel there is a slow reaction of the alkaline earth metal salt with the soluble alginate for otherwise an insoluble fibrous alginate may well form. The amount of alkaline earth metal salt will generally be about 30 to 65 percent by weight of the soluble alginate. The preferred metal salt is dibasic calcium phosphate which will produce a calcium alginate gel.

The gel may also be produced by bringing together a soluble alginate such as sodium alginate, and a pre-swelled bentonite and allowing the alkaline earth metal ions of the bentonite to react with the soluble alginate and form an alkaline earth metal alginate gel. In this manner a calcium, magnesium or mixed calcium/magnesium alginate gel may be produced. This is the preferred method because bentonite is a good and economic slow release source of alkaline earth metal ions. Further the gel is a more stable gel than that produced using an alkaline earth metal salt. Bentonite is a montmorillonite which swells when wetted with water. The weight ratio of the soluble alginate to bentonite is preferably in the range 1:1 to 1:10.

The soluble alginate may be produced by boiling seaweed in an alkaline salt solution, such as a sodium carbonate solution, milling the thus treated seaweed, and then removing, e.g. by filtration, large insoluble particles, e.g., insoluble particles having a particle size greater than 150 microns.

The gel may be treated, e.g. by filtration, to remove insoluble particles having a particle size greater than 70 microns. The resulting product is a coloured alginate gel containing at least 0.05 percent, generally at least 0.5 percent, by weight of insolubles having a particle size less than 70 microns. These insolubles will be from the seaweed or the seaweed and the bentonite when bentonite is used in the manufacture of the gel. Such a gel, while suitable for agricultural applications, is totally unsuitable for food applications.

The composition of the invention may also contain a wetting agent. The wetting agent assists in improving the spreadability of the composition on the surface to which it is applied. The preferred wetting agent is an anionic surface surfactant. Non-ionic surfactants may also be used. Examples of suitable non-ionic surfactants are linear primary alcohol ethoxylates, polyoxyethylene dodecyl phenol, polyoxyalkylene nonyl phenol, polyoxyethylene octyl phenol, ethoxylated castor oil, polyoxyethylated sorbitol, polyoxyethylene stearate, sorbitan monolaurate, sorbitan monostearate and sorbitan monooleate. Examples of anionic surfactants are alkylaryl sulfonates, lauryl polyoxyethylene salts, dioctyl sodium sulfosuccinate, salts of lignosulfonic acids, salts of sulfate ester of nonylphenoxypoly (ethylenoxy) ethanol, polyoxyethylene nonylphenol phosphate esters, tall oil and salts of alkyl sulfates.

The composition of the invention may also include an active ingredient such as a herbicide, pesticide, fertilizer, fungicide or the like. The amount of active ingredient present will vary according to the nature of the active ingredient and the application to which the composition is to be put. Examples of active ingredients are mancozeb, paraquat, fenthion, malathion, and the like.

The composition of the invention will typically be applied to a soil or plant locus by spraying. To this end, the composition will generally be diluted with water to the desired concentration. The dilution will vary according to the application.

In one particular form of the invention, the composition includes a thripsicide such as a salt of an antimony carboxylic acid having an alpha monohydroxy group or nicotine sulphate. The preferred thripsicide is tartar emetic which has the chemical name potassium antimony tartrate. The composition is applied to citrus fruit where thrips, also known as *Scirtothrips aurantii sauri*, causes considerable damage to citrus fruit by eating the tissue around the calyx when the fruit is still young and small. This damage then heals as a scar which stretches as the fruit grows and causes unsightly discolouration to the skin around the calyx. In many cases these fruits are unsaleable. The composition containing the thripsicide is applied to the citrus trees. The alginate gel provides a non-phytotoxic protective coating for the thripsicide active ingredient which nevertheless allows the thripsicide to function effectively.

The composition of the invention has been found to be particularly effective, when diluted with water, for fire fighting, particularly for the control and extinguishing of forest fires. The composition may be applied to the burning trees or ahead of the burning trees to prevent spread of the fire. The composition will preferably contain the alginate gel, a foaming agent and optionally also a wetting agent. The foaming agent may be an agent such as a lauryl ether sulphate, e.g. sodium lauryl ether sulphate, and the wetting agent may be any of the wetting agents described above. The preferred amounts of each component added to 2000 liters of water are:

Alginate gel - 25 to 200 liters, preferably 40 to 70 liters.

Foaming agent - at least 500 grams, typically 1 kg to 5 kg.

Wetting agent - 300 to 700 grams.

Typical uses and compositions of the invention are set out in Table 1.

TABLE 1

| Use | Composition Alginate Gel (% by weight) | Composition Wetting Agent (% by weight) | Dilution In Use (Amount of Composition Added to 100 l Water) | Active Ingredient |
| --- | --- | --- | --- | --- |
| Thripsicide | 100 | 0 | 250 to 1000 ml | Tartar emetic 400 g plus sugar 400 g |
| Red Spider Remedy | 40 to 75 | 0.5 to 1 | 1 to 5 l | Organophosphate (optional) |
| Soil Penetration Inhibitor | 30 to 60 | 1 to 30 | 50 to 250 ml | Atrazine |
| Forest Fire Fighting | 88 to 98.5 | 0.5 to 2 | 1.25 l to 10 l | Foaming Agent |
| Wetter/ Sticker Adjuvant for Sprays | 30 to 60 | 10 to 30 | 50 to 250 | Trace Elements Fungicide, Pesticide or Herbicide |

COMMENTS

1. The sugar which is added to the thripsicide is present as a bait.

2. For the red spider remedy, the composition when diluted is applied to an infested locus and in effect acts to drown the pest. Thus, the organophosphate or other active ingredient is optional.

3. For soil penetration, the composition of the invention acts to retain water in the surface of soil to which it is applied, particularly sandy soils. Thus, if an active ingredient such as atrazine is applied to a crop, residual atrazine which falls on the soil is held there and any leaching thereof is reduced.

The invention will be illustrated further by the following specific examples.

EXAMPLE 1

A mixed calcium and magnesium alginate gel was made in the following manner. Seaweed of the *Laminaria* type was brought to the boil with sodium carbonate solution and then milled in a high shear mixer to produce a slurry containing the milled seaweed. The slurry contained approximately one percent by weight sodium alginate. The slurry was filtered to remove insoluble weed body having a particle size greater than 150 microns. To the filtered slurry was added finely particulate bentonite which had been pre-swelled with water to give a composition containing about 8 percent by weight bentonite. The bentonite had the following composition:

| | |
| --- | --- |
| $SiO_2$ | 60.99% |
| $Al_2O_3$ | 20.30 |
| $Fe_2O_3$ | 6.16 |
| $TiO_2$ | 0.35 |
| CaO | |
| MgO | 7.43 |
| $Na_2O$ | |
| $K_2O$ | 3.73 |
| MOISTURE | 9.9 |

Ion exchange occurred over a period of about 30 minutes producing a mixed calcium and magnesium alginate gel of good gel strength. The thus produced gel was filtered again to remove insolubles having a particle size greater than 70 microns. The final composition was as follows:

| Component | Amount (per 250 l) |
| --- | --- |
| Alginate (predominantly calcium) | 1.3 kg |
| Bentonite | 6.0 kg |
| Water | 241 l |
| Other seaweed solubles & insolubles | 2.0 kg |
| | 0.2 kg |

EXAMPLE 2

A mixed calcium and magnesium alginate gel in a water base was made in the manner set out in Example 1 except the seaweed used was of the *Ecklonia Max.* type.

EXAMPLE 3

The composition of Example 1 had added to it sodium dioctyl sulfosuccinate (a wetting agent), silicon 1520 (a de-foamer from Dow Corning) and acetic acid. The final composition had the following constituents:

| Ingredient | Percent by Weight |
| --- | --- |
| Sodium Dioctyl Sulfosuccinate | 10 |
| Alginate Gel | 20 |
| Silicon 1520 | 0.4 |
| Acetic Acid | to pH 7.2 |
| Water | balance |

This composition was an excellent wetter/sticker adjuvant for various spray applications and can be used in the manner set out in Table 1 above.

EXAMPLE 4

250 ml of a composition as produced in Example 1 was added to 100 l water. Also added to the water was tartar emetic and sucrose each in an amount of 400 g. The diluted composition was thoroughly mixed. The composition was then delivered to a spray nozzle for application to a citrus crop. It was found that an excellent application of the composition to the citrus crop was achieved with the composition being firmly adhered to the leaves and fruit of the trees. Further, good control of the thrips was achieved. It was noted that the composition was not removed by rain from the trees.

EXAMPLE 5

A solution was made of sodium alginate, sucrose and tartar emetic by dissolving the various components in water. Each of the components was provided in an amount of 400 g per 100 l. 200 g of finely divided dibasic calcium phosphate was dispersed in 1 l of water. The dispersion was added to the solution and the mixture delivered to a spray nozzle for application to a citrus crop. On delivery of the mixture to the spray nozzle the gel began to form. However, by the time the mixture was sprayed on to the crop, gelling had not ocurred to an extent whereby the nozzle became blocked. The formation of a calcium alginate gel was completed soon after application to the crop. The coating for the crop which was obtained consisted of a calcium alginate gel which was non-phytotoxic and substantially water-insoluble and included the tartar emetic and the sucrose. The gel did not in any way affect the efficacy of the tartar emetic in controlling the thrips.

EXAMPLE 6

A composition useful, when added to water, in fire fighting consists of the following:
1. Alginate gel - 48 liters. The alginate gel was as produced in Example 1.
2. Sodium lauryl ether sulphate - 1 kg.
3. Sodium dioctyl sulfosuccinate - 0.5 kg.

This composition had a volume of about 50 liters and was added to 2000 liters of water. The water, with the composition added to it, was dropped from an aeroplane on to an area of burning pine trees. The falling water formed droplets which were found to be large and have a size distribution within a narrow band, thus allowing the water to be concentrated on the area of the burning trees. The fire was effectively extinguished and did not start again. In contrast, a similar area of burning pine trees was only partially extinguished with the same amount of water, also containing the foaming and wetting agents, but not the alginate gel, and started again soon after spraying.

I claim:

1. A thixotropic composition for application to a plant locus, comprising
    a gel comprising water, an alkaline earth metal alginate gel matrix uniformly dispersed throughout the water, bentonite, and at least about 0.05 percent by weight of insolubles having a particle size less than about 70 microns, wherein the weight ratio of the alginate gel to the bentonite is about 1:1 to 1:10, the water is present in an amount of at least about 90 wt % of the gel and the alginate gel matrix is present in an amount of up to about 5 wt % by weight of the gel.

2. The thixotropic composition of claim 1, wherein the alkaline earth metal alginate is selected from the group consisting of calcium, magnesium alginate and mixtures thereof.

3. The thixotropic composition of claim 1, further comprising
    a wetting agent.

4. A thixotropic composition of claim 3, wherein the wetting agent comprises an anionic surfactant.

5. The thixotropic composition of claim 1, further comprising
    a foaming agent.

6. The thixotropic composition of claim 5, wherein the foaming agent is present in an amount of about 1 to 10 weight percent of the composition.

* * * * *